United States Patent [19]

Oberhardt et al.

[11] 4,097,237
[45] Jun. 27, 1978

[54] DETERMINATION OF CELLS IN BLOOD

[75] Inventors: Bruce J. Oberhardt, Hartsdale; Jack Olich, Mahopac, both of N.Y.

[73] Assignee: Technicon Instruments Corporation, Tarrytown, N.Y.

[21] Appl. No.: 774,560

[22] Filed: Mar. 4, 1977

[51] Int. Cl.$^2$ .................... G01N 21/02; G01N 31/02; G01N 31/22; G01N 33/16
[52] U.S. Cl. ........................................ 23/230 B; 195/1
[58] Field of Search ..................... 23/230 B; 73/64.1; 195/1

[56] References Cited

U.S. PATENT DOCUMENTS

| | | | |
|---|---|---|---|
| 3,334,018 | 8/1967 | Smythe | 23/230 B |
| 3,427,135 | 2/1969 | Pelavin et al. | 23/230 B |
| 3,627,495 | 12/1971 | Adler, Jr. et al. | 23/230 B |
| 3,648,160 | 3/1972 | Beaver | 23/230 B |
| 3,684,450 | 8/1972 | Adler et al. | 23/230 B |
| 3,902,964 | 9/1975 | Greenspan | 23/230 B |

OTHER PUBLICATIONS

Hemolysis and Related Phenomena; Eric Ponder, Grune & Stratton, New York 1948, pp. 51-53.
A New Method for the Detection of Red Cell Antitbodies, Parviz Allezari, Automation in Analytical Chemistry, Technicon Symposium, vol. 1, 1967.

Primary Examiner—Morris O. Wolk
Assistant Examiner—Michael S. Marcus
Attorney, Agent, or Firm—S. P. Tedesco

[57] ABSTRACT

A method for determining a volume of red cells in a blood sample. The method includes the steps of flowing along a conduit a predetermined volume of the sample, introducing an agglutinating reagent and a predetermined volume of a dye into the conduit to mix with the sample and agglutinate the red cells, the dye being of known concentration on the introduction thereof, decanting the agglutinated red cells from the conduit, and colorimetrically measuring the concentration of the dye in the conduit, the agglutinating reagent being characterized by a relatively high positive electrical charge and the dye being water soluble and characterized by not penetrating said cells and not forming a precipitate with the agglutinating reagent or with the soluble components of the sample and not lysing the cells or altering the volume of the cells.

11 Claims, 1 Drawing Figure

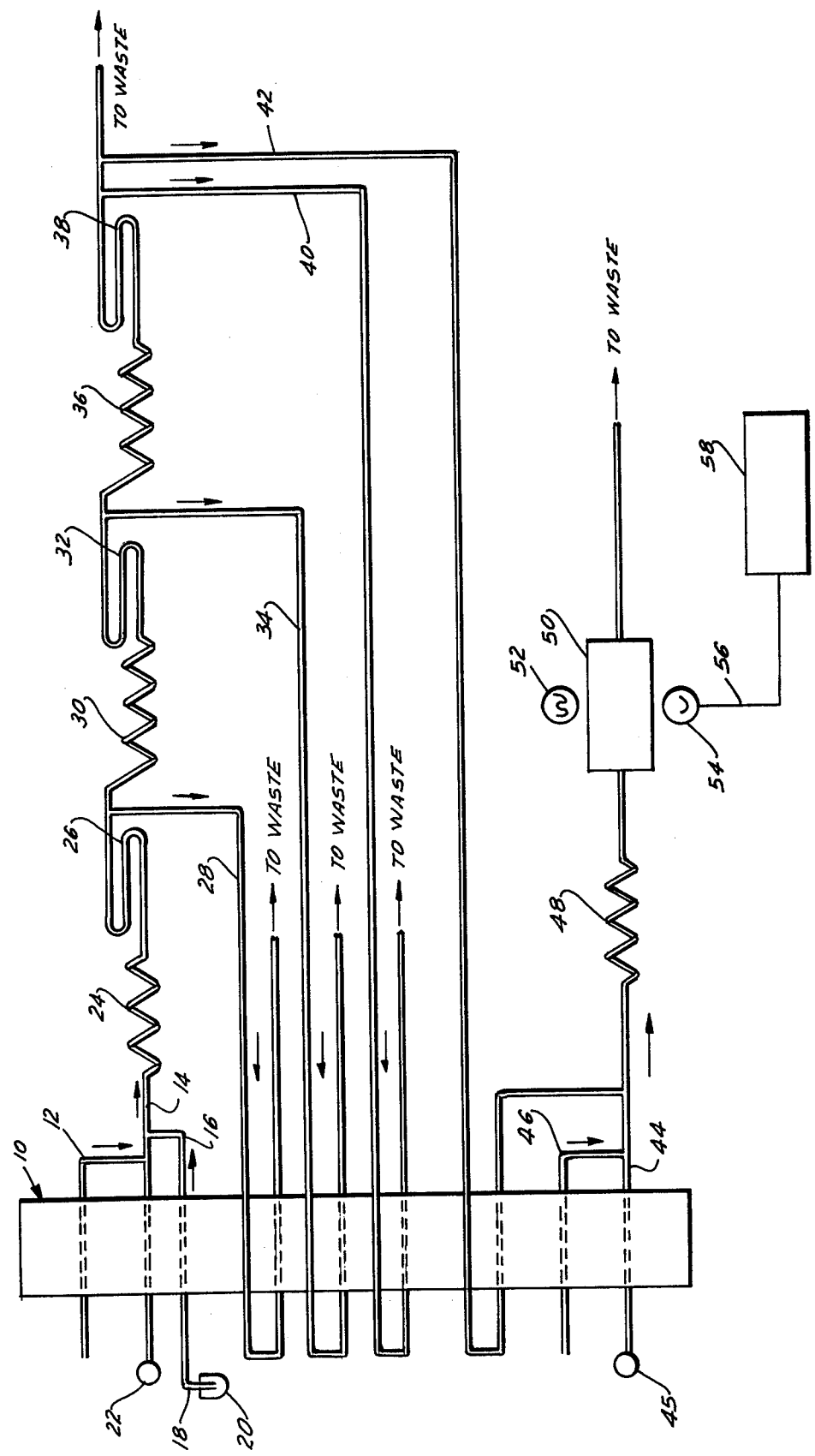

DETERMINATION OF CELLS IN BLOOD

This invention relates to a colorimetric determination of a volume of red cells in a blood sample, and relates more particularly to an improvement of a well-known technique for such a determination based on use of a dye which, when added to a blood sample, is excluded from the cell portion and colors the plasma portion. The greater the color density of the plasma portion in the sample when centrifuged, the greater the percentage of cell volume in the sample, according to that technique described by Eric Ponder, *Hemolysis and Related Phenomena*, Grune & Stratton, New York 1948, pp. 51–53. Basically, the colorimetric technique disclosed by Ponder comprises the addition of a known volume of a dye at a known concentration to a known volume of a blood sample of unknown cell volume. The technique includes separation of the sample liquid (plasma) from the cells by centrifugation of the sample, and colorimetric determination of the dye concentration in the plasma. Given the final dye concentration in the plasma, the initial dye concentration, and the volumes of sample and dye, the volume of red cells is then calculated. A significant advantage of the present invention is that centrifugation of the sample is avoided.

Accordingly, one object of the invention is to provide an improved colorimetric method for the determination of the volume of red cells in a blood sample utilizing a dye. Another object is to provide such a technique which is applicable to liquid sample analysis of the continuous-flow type. There is provided a method for determining a volume of red cells in a blood sample comprising the steps of flowing along a conduit a predetermined volume of the sample, introducing an agglutinating reagent and a predetermined volume of a dye into the conduit to mix with the sample and to agglutinate the red cells, the dye being of known concentration on the introduction thereof, decanting the agglutinated red cells from the conduit, and colorimetrically measuring the concentration of the dye in the conduit, the agglutinating reagent being characterized by a relatively high positive electrical charge and the dye being water soluble and characterized by not penetrating the cells and not forming a precipitate with the agglutinating reagent or with the soluble components of the sample and does not lyse the cells or alter the volume of the cells.

In the drawing, apparatus is shown schematically for carrying out the method of the invention.

In the drawing, there is shown a pump 10, which may be of the peristaltic type, which has compressible pump tubes 12, 14 and 16 extending therethrough. Coupled to the inlet of tube 16 is the outlet end of a sample probe 18 having an inlet end for imersion in each of a series of sample cups containing different live whole blood specimens to which an anticoagulant was added, one such cup being shown at 20. Such sample cups may be presented sequentially to the probe 18 for offtake of their contents through pump tube 16. Pump tube 14 has an inlet end connected to a liquid reservoir 22 which supplies an agglutinating reagent in a mixture with a dye, which substances will be described more fully hereinafter. Pump tube 12 has an inlet end open to the atmosphere for the supply of air through the tube 12. The outlet end of tube 12 is coupled to the tube 14 downstream from the pump 10 to deliver such air to the stream of the reagent and dye mixture in the tube 14, segmenting such stream. The outlet of the tube 16 is coupled to the tube 14 as shown to add sample to the aforementioned segmented stream. The stream of the combined substances is flowed through a mixing coil 24 interposed in tube 14 to mix such substances together. As a result of such mixing, the red cells of the sample are agglutinated. Subsequent to such agglutination, the stream is passed from the coil 24 through a settling coil 26 interposed in tube 14, wherein the agglutinated red cells settle out from the mixture. Downstream from the coil 26 a decanter tube 28 of a nonillustrated conventional decanter fitting has an inlet end coupled to the tube 14, the tube 28 being compressible and extending through the pump 20 to empty to waste. Almost all the agglutinated cells in the tube 14 are decanted from the tube 14 through the tube 28.

The remainder of the stream in the tube 14 flows through interposed mixing coil 30 where remaining free red cells are again mixed with the agglutinating reagent. The stream passes from the coil 30 in the tube 14 to a second settling coil 32 interposed in the tube 14 where remaining agglutinated cells are settled. Downstream from the coil 32, a decanter tube 34, similar to the tube 28, has an inlet end coupled to the tube 14, the tube 34 being compressible and extending through the pump 20 to empty to waste. Tube 34 carries off previously agglutinated cells from the tube 14. The remainder of the stream in the tube 14 flows through a mixing coil 36 wherein any remaining red cells in the sample are again mixed with the agglutinating reagent for the agglutination of these cells. The stream then passes through the tube 14 to a third settling coil 38 for the separation of agglutinated cells from the mixture. Downstream from the coil 38, a compressible decanter tube 40 has an inlet end coupled to the tube 14, the tube 40 extending through the pump 20 and emptying to waste. The tube 40 decants the remaining agglutinated cells from tube 14. Downstream from the junctions of tubes 14 and 40, a compressible pump tube 42 has an inlet end coupled to the tube 14 to withdraw a portion of the remainder stream in the tube 14, the tube 42 extending through the pump 20 as shown. The portion of the remainder stream which is not removed through the tube 42 passes to waste in the tube 14.

Compressible pump tubes 44 and 46 extend through the pump 20. The tube 44 has an inlet end coupled to a reservoir 45 of diluent such as saline for supply to the tube 44. The tube 46 has inlet end open to atmosphere, the outlet being coupled to the tube 44 downstream from the pump, segmenting the flow of diluent with air segments. Downstream from the junction of the tubes 44 and 46, the outlet end of the aforementioned tube 42 is coupled to the tube 44 to add to the stream in the latter the stream from the tube 42. There are essentially no red cells flowing through the tube 42, these cells having been agglutinated and decanted from the tube 14. The flow in the tube 42 comprises plasma from the sample and the aforementioned dye. The aforementioned substances flowing in the tube 44 are mixed in coil 48 interposed therein and then flow through a colorimetric flowcell 50 interposed in the tube 44. Associated with the flowcell in the usual arrangement are a light source 52 and a photodetector 54. The detector 54 has an output along lead 56 to a conventional recorder 58 displaying the concentration of the dye detected in the flowcell 50. As the volume of the sample is predetermined and known, together with the volumes of the other aforementioned substances, and the concentration of the dye in the reservoir 22 is known, the percentage volume of the red cells of the sample may be calculated in a conventional manner. The calculation is subject to an error to the extents of white cells present in the sample, but the error is insignificant in blood specimens not having an abnormally high number of white cells. By way of illustration only, pump tubes 12, 14, 16, 28, 34 and 40 may have flow rates of 0.42, 0.80, 0.80, 0.60, 0.16 and 0.16 ml/min, respectively. Similarly, pump tubes 42, 44 and 46 may have flow rates of 0.16, 4.0 and 0.32 ml/min, respectively. The aforementioned dilutent added to the tube 44 is supplied to add volume to the stream from the tube 42 and reduce noise in the measurement of the dye concentration.

It is of importance that the dye and the agglutinating reagent be nonreactive with one another and that the dye not adhere to or enter the red cells. For agglutinating red cells, a reagent such as a cationic polyelectrolyte or protamine may be used. Such a cationic polyelectrolyte is available from Aldrich Chemical Co. under the trademark Polybrene. A nonproprietary name for this substance is hexadimethrine bromide. This agglutinating reagent has a relatively high positive electrical charge to react with red blood cells which have a relatively high negative electrical charge. If desired, a panagglutinating antibody may be used to agglutinate the red cells, such as goat or rabbit anti-human red blood cell antibody or other agglutinating agents such as plant lectins.

Ponder, supra, mentions the use of two dyes, neither of which is suitable in the present method for determination of a volume of red cells, polybrene, for example, reacts with Evans Blue (Eastman Kodak), Ponder's choice of a dye, to form a precipitate. Such reaction would render the present method unworkable. Hemoglobin is Ponder's second choice of a dye. However, a natural product of blood cells, such as hemoglobin allows artifacts to appear in the dye concentration measurement. For example, when hemoglobin is used as a dye, possible leakage of the donor's hemoglobin from the red cells or high hemoglobin levels in the plasma due to introvascular hemolysis may contribute to the hemoglobin dye and produce erroneous results in the colorimetric measurement. In accordance with the present method, the selected dye, meeting the aforementioned characteristics, must be water soluble and have a relatively low electrical charge. Further, because hemolysis of red cells is a natural process, the dye should be of a color other than red. We have found that a suitable dye for use in the above-described method may be suitable diphenyl or triphenyl substituted methane derivative such as Erio Blue Glassine A, also known as triphenylmethane 42090, or may be a dye such as Fast Green FCF, for example.

While the presently preferred embodiments of the method for determining red cell volume have been described, it will be apparent, especially to those versed in the art, that the method may take other forms and is susceptible to changes in details without departing from the principles of the invention.

What is claimed is:

1. A method for determining the volume of red cells in a blood sample comprising:
   flowing along a conduit a predetermined volume of said sample;
   introducing a known volume of an agglutinating agent and a predetermined volume of a dye into said conduit, said agglutinating agent being characterized by a relatively high positive charge, said dye being of a material not present in blood samples of the type being determined, said dye also being of known concentration and water soluble and characterized by (1) not penetrating said cells, (2) not forming a precipitate with said agglutinating agent or with soluble components of said sample, and (3) not lysing said cells or altering the volume of said cells;
   mixing at least said sample and agglutinating agent while flowing along said conduit to agglutinate the red cells;
   decanting the agglutinated red cells from said conduit; and
   colorimetrically measuring the concentration of said dye in the plasma flowing along said conduit.

2. A method as defined in claim 1, wherein: said agent is a cationic polyelectrolyte.

3. A method as defined in claim 1, wherein: said agent is a protamine.

4. A method as defined in claim 1, wherein: said agent is a hexadimethrine bromide.

5. A method as defined in claim 1, wherein: said dye is Erio Blue Glassine A.

6. A method as defined in claim 1, wherein: said dye is Fast Green FCF.

7. A method as defined in claim 1, further including introducing a gas into said conduit to segment the liquid stream therein.

8. A method as defined in claim 1, wherein: said agent and said dye are introduced from a common reservoir.

9. A method of determining the red cell volume in a blood sample comprising the steps of:
   introducing a known volume of an agglutinating agent into a known volume of said sample, said agglutinating agent being characterized by a relatively high positive charge;
   introducing a known volume of dye into said sample volume, said dye being of a material not present in blood samples of the type being determined said dye also being of known concentration and water soluble and characterized by (1) not penetrating said cells, (2) not forming a precipitate with said agglutinating agent or with soluble components of said sample, and (3) not lysing said cells or altering the volume of said cells;
   separating the agglutinated red cells within said sample volume; and
   colorimetrically measuring the concentration of dye in the plasma of said sample, to provide an indication of its red cell volume.

10. A method as defined by claim 9 wherein: said agglutinating agent is a panagglutinating antibody.

11. A method as defined in claim 9 wherein: said agglutinating agent comprises plant lectins.

* * * * *